United States Patent [19]

Johnson

[11] Patent Number: 4,558,035

[45] Date of Patent: Dec. 10, 1985

[54] MATERIAL FOR USE IN THE TREATMENT OF SPONTANEOUS ABORTIONS

[75] Inventor: Peter M. Johnson, Wirral, England

[73] Assignee: The University of Liverpool, Liverpool, England

[21] Appl. No.: 584,420

[22] Filed: Feb. 28, 1984

[30] Foreign Application Priority Data

Mar. 4, 1983 [GB] United Kingdom ............... 8305967

[51] Int. Cl.[4] ................... A61K 35/50; A61K 37/02; A61K 39/00
[52] U.S. Cl. .................................. 514/8; 260/112 R; 260/112 B; 424/88; 424/101; 424/105; 514/21
[58] Field of Search ....................... 260/112 R, 112 B; 424/177, 101, 105, 88; 514/8, 21

[56] References Cited

PUBLICATIONS

Journal of Reproductive Immunology, 2 (1980), 99–108; 1 (1979), 127–140, Ogbimi et al.

American Journal of Reproductive Immunology, 1: 246–254, (1981), Johnson et al.
Lancet, vol. II, 1981, pp. 68–70, Taylor et al.
Nature, 252, (1974), 302–303, Smith et al.

*Primary Examiner*—Howard E. Schain
*Attorney, Agent, or Firm*—Beveridge, DeGrandi & Weilacher

[57] ABSTRACT

This invention relates to a material for use in preventing recurrent spontaneous abortions in women, comprising material selected from isolated syncytiotrophoblast microvillous plasma membrane and protein- and glycoprotein-containing fractions derived therefrom.

The invention also relates to a method for preventing recurrent spontaneous abortions in women, the method comprising administering to a woman a material comprising material selected from isolated syncytiotrophoblast microvillous plasma membrane and protein- and glycoprotein-containing fractions derived therefrom.

5 Claims, No Drawings

MATERIAL FOR USE IN THE TREATMENT OF SPONTANEOUS ABORTIONS

DESCRIPTION

The present invention relates to a material for use in the treatment of human spontaneous abortions. More particularly, the present invention relates to a material for use in the prevention of recurrent spontaneous abortions in women, the material being isolated placental trophoblast membrane.

It is known that if a pregnant woman suffers a spontaneous abortion then any subsequent pregnancies which that woman may have are also more likely to result in spontaneous abortions. The precise reason why certain women suffer such spontaneous abortions is not known but an immunological defect is suspected in many cases of recurrent spontaneous abortion for which no underlying genetic, hormonal, microbiological or anatomical abnormality has been detected. This defect is now thought to be related to a failure of maternal immune recognition of the implanting blastocyst, which results in the lack of production of protective factors and subsequent rejection of the developing foetal trophoblastic tissue at maternal-foetal interfaces. Trophoblast is the lining cell of the foetal placenta and of the foetal membranes surrounding the conceptus throughout gestation. It is, therefore, the only and continuous point of contact of the foetal tissue with the maternal host throughout pregnancy.

The nature of the cell surface antigen complex that is recognised immunologically by the mother in healthy pregnancy but which the women who suffer recurrent spontaneous abortions fail to recognise, is not fully known. However, it is thought not to be any of the white cell or red cell surface antigens at present routinely investigated in clinical medicine. Nevertheless, there is evidence that at least a proportion of the white cells (leucocytes) of the blood express the relevant antigen. Thus, planned immunisation with unmatched (i.e. genetically dissimilar or tissue-type dissimilar) concentrates of blood white cells has been used successfully to prevent subsequent spontaneous abortions in habitually aborting woman (see Taylor, C. & Faulk, W. P., The Lancet, ii, (1981), 68–70, and Beer, A. E., Quebberman, J. F., Ayeres, J. W. T. and Haines, R. F., Amer. J. Obs. Gynec., 141 (1981), 987–999). However, there may be clinical problems with this procedure in that occasional off-spring born of such pregnancies may be at risk of an immunodeficiency disease resulting from transplacental passage of maternal immune cells to the developing conceptus in utero; this being due to maternal immune sensitization to other cell surface antigens, defined by the major histocompatibility gene complex (MHC), which are expressed on blood leucocytes (but not on trophoblast).

In healthy pregnancy, however, the cellular source stimulating protective immune responses without any deleterious effect is provided by the foetal tissue directly exposed to maternal blood and tissue components of the immune system - that is, specifically, the surface of the lining cell of the human placenta, termed the syncytiotrophoblast microvillous cell membrane. This cell surface membrane expresses the relevant antigen concerned with stimulating a protective immune response in pregnancy but does not express the other, potentially harmful, MHC antigens. Methods have already been developed for isolating this membrane in very high purity away from whole placental tissue (see Smith, N. C., Brush, M. G. and Luckett, S. Nature, 252 (1974), 302–303. These methods have been employed and developed extensively by the Applicant, who has acquired probably the most detailed experience on their biochemistry and laboratory handling procedures.

The isolated syncytiotrophoblast microvillous cell membrane, which has been termed "StMPM" (syncytiotrophoblast microvillous plasma membrane), comprises small vesicles of lipid membrane containing associated proteins and glycoproteins on their surface. Up to the present time, isolated placental StMPM has only been used in laboratory research work and has not been used in any medical application.

It has now been found that prior immunization with placental StMPM may be used successfully to stimulate the necessary protective immune response for successful pregnancy to term in women who previously have not adequately responded to trophoblast membranes derived from their implanted blastocyst and who are, therefore, likely to suffer recurrent spontaneous abortions.

According to the present invention there is provided a material for use in the prevention of recurrent spontaneous abortions in women, characterised in that the material comprises material selected from isolated syncytiotrophoblast microvillous plasma membrane and protein- and glycoprotein-containing fractions derived therefrom.

As used hereinafter, the abbreviation "StMPM" is intended to refer to isolated syncytiotrophoblast microvillous plasma membrane and to protein- and glycoprotein-containing fractions derived therefrom.

According to the present invention there is also provided a method for preventing recurrent spontaneous abortions in women, characterised in that it comprises administering to a woman a material comprising material selected from isolated syncytiotrophoblast microvillous plasma membrane and protein- and glycoprotein-containing fractions derived therefrom.

The StMPM is administered, preferably by intravenous infusion, to a woman who is known to suffer, or who is believed to be likely to suffer, recurrent spontaneous abortions. It is contemplated that StMPM may be administered, as a general procedure, to any woman who has suffered an abortion which may be due to a failure of maternal immune recognition and a failure to produce protective responses such that, if the abortion has indeed been due to a failure of maternal immune recognition and a failure to produce protective responses, the early loss of any subsequent pregnancies of that woman by the same man will be prevented.

Since the purpose of StMPM is to stimulate, in women who are likely to suffer recurrent spontaneous abortions, the necessary maternal immune recognition and production of protective responses for successful continuance to term of pregnancy, it will be readily evident that StMPM must not have been isolated from the woman to whom it is to be administered but must have been isolated from a different woman or different women.

StMPM, for example, be derived following collecting randomly, at source, healthy placentae from normal pregnancies in women of known blood-group, placing these placentae in sterile containers, and then processing the placental villous tissue by cold saline extraction and ultracentrifugation to isolate StMPM (see Smith, N.

C. Brush, M. G. and Luckett, S. Nature, 252, (1974), 302–303, and Ogbimi, A. O., Johnson, P. M. Brown, P. J. and Fox, H., J. Reprod. Immunol, 1 (1979), 127–140).

The isolation of StMPM from whole placentae by cold saline extraction and ultracentrifugation comprises dicing fresh placental villous tissue, washing the diced placental tissue rapidly in cold (e.g. 0° C. to 4° C.) isotonic calcium chloride solution or other buffer at neutral pH to remove base blood and then gently agitating the diced placental tissue in cold (e.g. 0° C. to 4° C.) isotonic saline at neutral pH, for example, for a period of approximately 60 minutes. The resulting mixture is then filtered and the filtered solution obtained is centrifuged at 600 to 1,000 g, preferably at approximately 800 g. The duration of this centrifugation may, for example, be approximately 10 minutes. The solution obtained is then centrifuged at least once at 10,000 to 15,000 g for a period of, for example 10 to 30 minutes. Following this, the supernatant obtained (containing suspended StMPM vesicles) is subjected to ultracentrifugation at at least 80,000, preferably at at least 100,000 g, for a period of, for example, approximately 60 minutes to yield a final cell membrane pellet (i.e. StMPM). This pellet is in the form of a wet pellet and may, possibly following further washing in saline, for example, be frozen for storage purposes.

It is important to utilise aseptic techniques throughout the above-described procedure for the isolation of StMPM. Therefore, the placental tissue is preferably placed in a sterile container immediately upon its collection at source and the tissue is preferably processed to obtain StMPM as soon as possible after its collection, thereby minimising the possibility of bacterial contamination of the tissue. Further, all manipulations carried out during the isolation of StMPM are preferably carried out in a sterile air-flow hood.

One or more bacteriostatic agents are preferably added to all of the solutions involved in the isolation of StMPM from whole placentae in order to minimise the possibility of bacterial contamination of the solutions and the final StMPM pellet. Also, it is preferable to sterilise the final isolated StMPM pellet, for example by U.V.—irradiation.

Alternatively to maintaining StMPM in the form of wet membrane pellets or frozen membrane pellets, these preparations may be lyophilised from their pelleted or resuspended solution form. The lyophilised powder may then be reconstituted prior to intravenous infusion. If the StMPM preparation is stored in the form of a lypholised powder, it is preferable, after reconstitution but before intraveous infusion, to remove grossly aggregated material.

The StMPM, which is to be administered to the woman by intravenous infusion, may, for example, be from a single StMPM preparation. However, it is also possible to administer StMPM derived from a pool of several such preparations. The biochemical characterization of such isolated StMPM has been described in detail by the applicant in the scientific literature (see Ogbimi, A. O., Johnson, P. M., Brown, P. J. and Fox, H., J. Reprod Immunol., 1, (1979), pages 127–140; Ogbimi, A. O., and Johnson P. M., J. Reprod Immunol, 2, (1980), pages 99–108, and an article by Johnson, P. M. in *Immunological Aspects of Reproduction in Mammals*, Edited by D. B. Crighton, published by Butterworth, 1984).

To allow StMPM to be intraveneously infused into the woman to whom it is to be administered, the StMPM pellet must be suspended in a suitable solution. For example, approximately 1 g of the wet StMPM pellet may be resuspended into a suitable solution, e.g. saline or buffered dextrose solution, to produce approximately 20 ml of solution which can then be intravenously infused into the woman to whom it is to be administered, for example, over a period of approximately 1 hour. Alternatively, this solution of approximately 20 ml containing StMPM may be added to a sterile saline or dextrose drip-pack and intravenously infused, preferably over a period of not less than 1 hour.

Before intravenous infusion of the StMPM-containing solution, it is preferably thoroughly resuspended and centrifuged, e.g. at approximately 5,000 g for approximately 10 minutes to remove grossly aggregated particles.

It is important that, since isolated StMPM is for medical administration, all such material should be free of bacterial contamination as well as the more commonly assayed viral infections, for example, hepatitis or herpes virus. Furthermore, the blood (ABO and Rh) group of each donor placenta (i.e. the placenta from which StMPM isolated) must be known and matched to be compatible with that of the recipient (i.e. the woman to whom StMPM is to be administered). Finally, the thromboplastic activity of isolated StMPM material should be checked prior to in vivo administration.

Efficacy of treatment of the woman by administration of StMPM can, of course, only properly be assessed functionally, i.e. by there being subsequent healthy term pregnancy. However, it is thought that by following the development of antilymphocyte and/or anti-StMPM antibodies (the latter being assessed by new sensitive immunological assays) helpful information may be provided.

The relevant functional antigen system within the whole StMPM preparations is not known. However, the Applicant has found it to be one of the StMPM membrane-associated protein or glycoprotein structures. Although there is no clinical need to fractionate further intact isolated StMPM prior to administration a protein- or glycoprotein-containing fraction derived therefrom may be used. It is believed that the relevant functional antigen system is represented on trophoblast and leucocytic cells by a protein which has a subunit molecular weight of from 30,000 to 40,000 daltons and which is recognised by its reactivity with two murine monoclonal antibodies known as H310 and H316. The monoclonal antibodies H310 and H316 are described by McLaughlin, P. J., Cheng, H. M., Slade, M. B., and Johnson P. M. in Int.J.Cancer, 30, 21–26 (1982), and by Johnson, P. M., Cheng, H. M., Molloy, C. M., Stern, C. M. M. and Slade, M. B. in American Journal of Reproductive Immunology, 1, 246–254, (1981).

The present invention will now be further illustrated by way of the following Example:

EXAMPLE

A woman, who had already had three consecutive spontaneous abortions by a single spouse with each abortion occurring within fourteen weeks of pregnancy, was treated with syncytiotrophoblast microvillous cell membrane (StMPM) according to the present invention.

This StMPM material was isolated from a single placenta according to the method given above, and 1 g, wet weight, of isolated StMPM pellet was resuspended in 20 ml buffered dextrose prior to addition to a 250 ml sterile saline drip-pack and intravenously infused over a period of 1½ hours. The woman, since treatment with the StMPM according to the present invention, became pregnant again after three months and has, at the present time, successfully passed 24 weeks of pregnancy. It is therefore, expected that a successful full term of the pregnancy will now be completed.

I claim:

1. A method for preventing recurrent spontaneous abortions in women, characterized in that the method comprises administering to a woman a material comprising material selected from isolated syncytiotrophoblast microvillous plasma membrane and protein and glycoprotein-containing fractions derived therefrom.

2. A method according to claim 1, characterized in that the material is administered to the woman intravenously.

3. A method according to claim 2, characterized in that the material is in the form of a suspension in a medium selected from saline and buffered dextrose solutions.

4. A method according to claim 1, characterized in that the material is administered to the woman in the form of a suspension produced by suspending approximately 1 g of a wet pellet of the material in approximately 20 ml of a medium selected from saline and buffered dextrose solutions, and the suspension is administered to the woman by intravenous infusion over a period of approximately 1 hour.

5. A method according to claim 1, characterized in that the material is administered to the woman in the form of a suspension produced by suspending approximately 1 g of a wet pellet of the material in approximately 20 ml of a medium selected from saline and buffered dextrose solutions, the suspension is added to a sterile drip-pack containing a fluid selected from saline and dextrose, and the contents of the drip-pack are then intravenously infused into the woman.

* * * * *